(12) United States Patent
Chen

(10) Patent No.: US 10,517,699 B2
(45) Date of Patent: Dec. 31, 2019

(54) ALVEOLAR MEMBRANE

(71) Applicant: MONTJADE ENGINEERING CO., LTD., Taichung (TW)

(72) Inventor: Jiunn-Liang Chen, Taichung (TW)

(73) Assignee: Montjade Engineering Co., Ltd., Taichung (TW)

( * ) Notice: Subject to any disclaimer, the term of this patent is extended or adjusted under 35 U.S.C. 154(b) by 0 days.

(21) Appl. No.: 15/784,643

(22) Filed: Oct. 16, 2017

(65) Prior Publication Data

US 2019/0110870 A1    Apr. 18, 2019

(51) Int. Cl.
A61C 8/00    (2006.01)

(52) U.S. Cl.
CPC ............ *A61C 8/008* (2013.01); *A61C 8/0028* (2013.01)

(58) Field of Classification Search
CPC ...... A61C 8/008; A61C 8/0028; A61C 8/0031
USPC .................................................. 433/172–176
See application file for complete search history.

(56) References Cited

U.S. PATENT DOCUMENTS

| | | | | |
|---|---|---|---|---|
| 5,513,989 A * | 5/1996 | Crisio | ................... | A61C 8/0031 433/173 |
| 5,906,489 A * | 5/1999 | Khazzam | ............. | A61C 8/0022 433/173 |
| 6,030,218 A * | 2/2000 | Robinson | ............. | A61C 8/0006 433/173 |
| 6,287,118 B1 * | 9/2001 | Naganuma | ........... | A61C 8/0031 433/173 |
| 9,775,689 B2 * | 10/2017 | Yun | ....................... | A61C 8/0031 |
| 2014/0199657 A1 * | 7/2014 | Moon | ................... | A61F 2/2803 433/173 |
| 2014/0248583 A1 * | 9/2014 | Rostami | ............... | A61C 8/0012 433/173 |
| 2014/0349251 A1 * | 11/2014 | Moon | .................. | A61C 8/0006 433/174 |
| 2017/0290645 A1 * | 10/2017 | Rostami | ............... | A61C 8/0006 |

FOREIGN PATENT DOCUMENTS

| TW | 201311218 A | 3/2013 |
|---|---|---|
| TW | 201332523 A | 8/2013 |

* cited by examiner

*Primary Examiner* — Matthew M Nelson
(74) *Attorney, Agent, or Firm* — Wang Law Firm, Inc.

(57) ABSTRACT

An alveolar membrane includes: a connecting portion being provided thereon with a through hole for an artificial toothroot to pass therethrough; a capping portion having its one end connected to the connecting portion and including a plurality of openings; and a fixing portion being located at an opposite end of the capping portion and having at least one digit that has a tip to be fixed in osseous tissue or between osseous tissue and soft tissue. With the connecting portion and the fixing portion at its two ends both fixed, the alveolar membrane firmly holds the osseous graft in position.

4 Claims, 5 Drawing Sheets

ALVEOLAR MEMBRANE

BACKGROUND OF THE INVENTION

Field of the Invention

The present invention relates to alveolar membranes used in dental implant surgery, and more particularly to an alveolar membrane that provides good fixation.

Related Prior Art

Generally, in the event that a tooth or more teeth are lost due to accidents, diseases or other reasons, the affected person's mastication and occlusion could be undermined in addition to his/her facial appearance. Thus, many dentists would recommend their patients to have dental prostheses to replace the missed teeth.

The traditional dental prostheses can be roughly divided into fixed and removable ones. The removable dental prosthesis, as the name implies, is configured to be settled in and removed from a patient's oral cavity from time to time, and is suitable for a patient who has more than one tooth missed. On the other hand, a fixed dental prosthesis is fixedly installed in a patient's oral cavity and not easily removed. Most of the existing fixed dental prostheses are in the form of a bridge, which uses health teeth flanking a defective tooth as its support. However, for mounting such a bridge, the two health teeth have to be seriously ground or the dental prostheses cannot be fitted.

Dental implant surgery as a remedy for tooth loss has been increasingly popular. It involves implanting an artificial toothroot into an edentulous area, and has high durability while needing not to damage any health tooth. However, the tissue at the edentulous area can become atrophic over time. On average, a 40-percent tissue atrophy can be seen after half a year. Once such atrophy makes the alveolar bone too thin to secure the implant, the dental implant surgery can be declared as failed.

To address the shortage of bone at the edentulous site, it is a common practice to perform bone augmentation surgery first as preparation. So-called bone augmentation surgery is an operation to fill where a defect is found with an osseous graft, such as an artificial tooth or an autogenous bone, and cover the osseous graft with an alveolar membrane to keep the osseous graft in shape and in position.

An existing alveolar membrane is a sheet with a predetermined shape and has a connecting portion and a capping portion. The connecting portion is provided with a connecting hole for combining with an artificial toothroot. The capping portion is provided with a plurality of holes and serves to cap the osseous graft. More details about conventional alveolar membrane products are disclosed in Taiwan Patent No. 201311218, Taiwan Patent No. 201332523, US Patent Application No. 2014/0199657 and US Patent Application No. 2014/0349251, and will not be repeated herein.

With the foregoing configuration, the conventional alveolar membrane only has the connecting hole at its one end combined with the artificial toothroot and leaves its opposite end hung without support. Such an unstable combination may bring adverse influence to the sequent bone augmentation surgery and in turn bring some worrying consequences to the dental implant surgery.

SUMMARY

The primary objective of the present invention is to provide an alveolar membrane that offer good fixation.

For achieving the foregoing objective, the present invention alveolar membrane comprises a connecting portion, being provided with a through hole for an artificial toothroot to pass therethrough; a capping portion, having its one end connected to the connecting portion and including a plurality of openings; and a fixing portion, being located at an opposite end of the capping portion and having at least one digit that includes a tip to be fixed at a predetermined site in human tissue.

In one embodiment, the connecting portion, the capping portion and the fixing portion are formed in a single sheet.

In one embodiment, a flexible portion is provided at a joint between the connecting portion and the capping portion and is formed by a plurality of slots arranged into a straight line.

In one embodiment, a flexible portion is provided at a joint between the capping portion and the fixing portion and is formed by a plurality of slots arranged into a straight line.

In one embodiment, the digit of the fixing portion is configured to be inserted into osseous tissue or between osseous tissue and soft tissue.

In one embodiment, the connecting portion has its width gradually increased from its one end toward the capping portion until its width is equal to that of the capping portion.

With the connecting portion and the fixing portion at its two ends of fixed to the artificial toothroot and human tissue respectively, the disclosed alveolar membrane provides good fixation that ensures an osseous graft to be firmly fixed to the predetermined site, thereby contributing to smooth dental implant surgery.

DETAILED DESCRIPTION

For further illustrating the means and functions by which the present invention achieves the certain objectives, the following description, in conjunction with the accompanying drawings and preferred embodiments, is set forth as below to illustrate the implement, structure, features and effects of the subject matter of the present invention.

Figure 1:
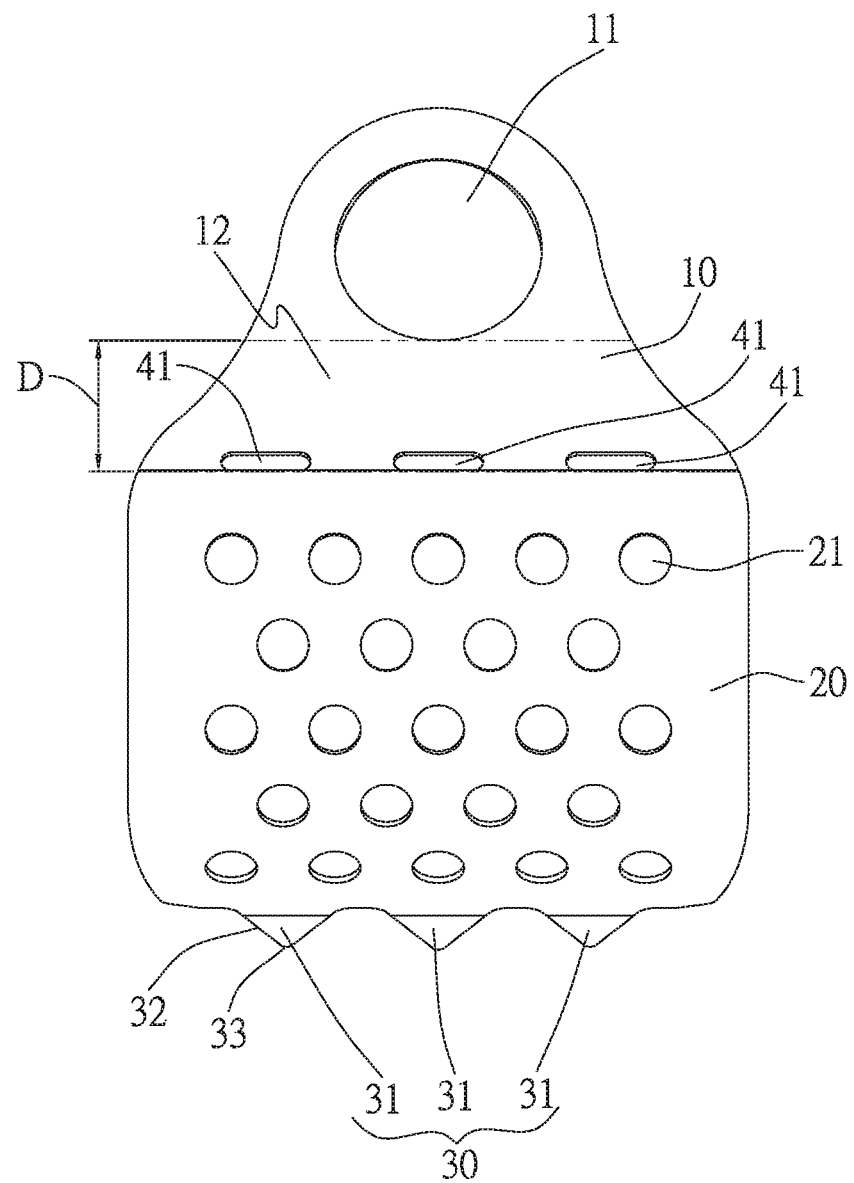
FIG. 1 is a font view of one preferred embodiment of the present invention.
Figure 2:
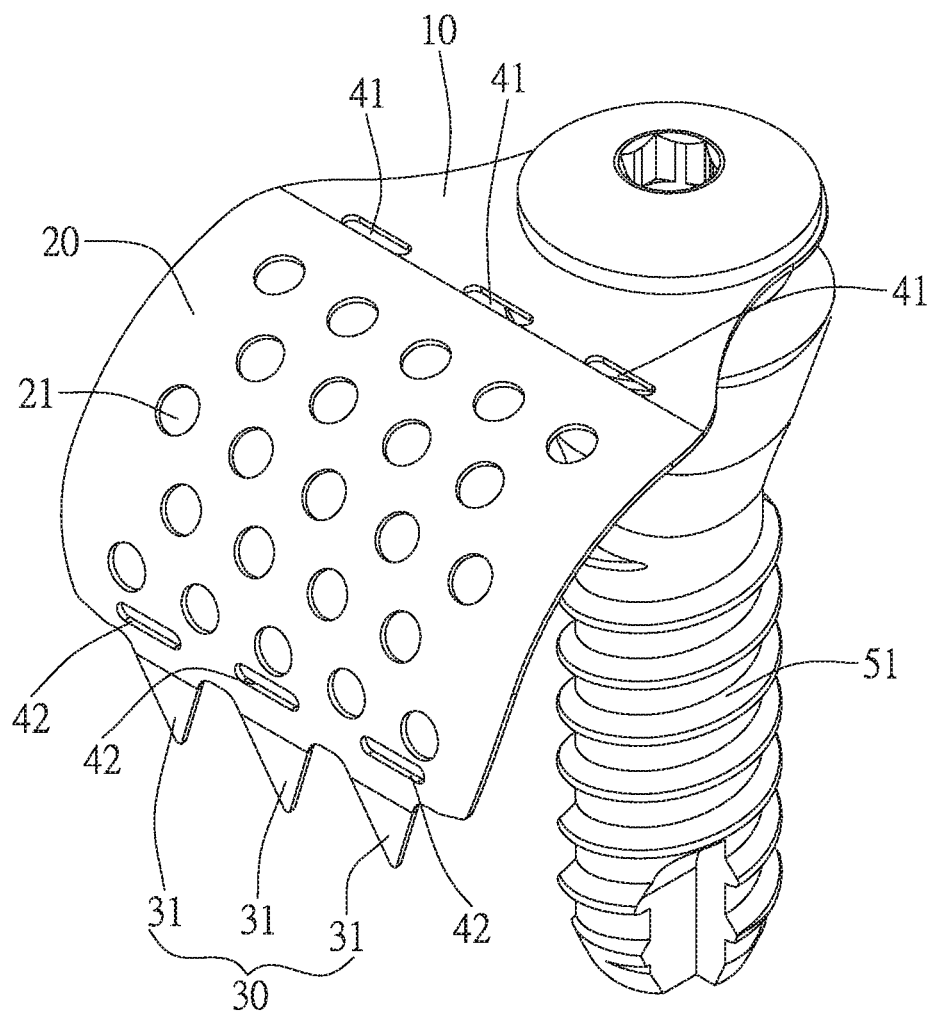
FIG. 2 is a perspective view of the preferred embodiment of the present invention, showing it combined with an artificial toothroot.

Referring to FIG. 1 and FIG. 2, in one preferred embodiment of the present invention, an alveolar membrane is a single sheet made of metal titanium, titanium alloy, or other suitable materials and is formed with a connecting portion 10, a capping portion 20, and a fixing portion 30 successively.

The connecting portion 10 has its width gradually increased from one end toward the capping portion 20 until its width is equal to that of the capping portion 20. The connecting portion 10 is provided with a through hole 11 for an artificial toothroot 51 to pass therethrough and then be fixed to an edentulous site. The connecting portion 10 includes a connecting area 12 which is located between the through hole 11 and the capping portion 20 to leave a distance D between the through hole 11 and the capping portion 20. The capping portion 20 has a predetermined radian and is provided with a plurality of round openings 21. The fixing portion 30 has three triangular digits 31. Each of the digits 31 has a sharp shape with two oblique edges 32. Each of the digits 31 has its outer end provided with a tip 33 which is located at an interconnection between the two oblique edges 32. In the present embodiment, the joint between the connecting portion 10 and the capping portion 20 and the joint between the capping portion 20 and the fixing portion 30 are each provided with a flexible portion. Each of the flexible portions is formed by three slots 41 or 42 arranged in a straight line, so that the connecting portion 10 and the capping portion 20 can be bent with respect to the capping portion 20 and the fixing portion 30 respectively for a predetermined angle.

Moreover, since the round openings 21 are located at the capping portion 20, and the connecting portion 12 is provided between the capping portion 20 and the through hole 11, so that the through hole 11 is separated from the capping portion 20 by the distance D, which ensures that there is no round openings 21 near the through hole 11.

Figure 3:
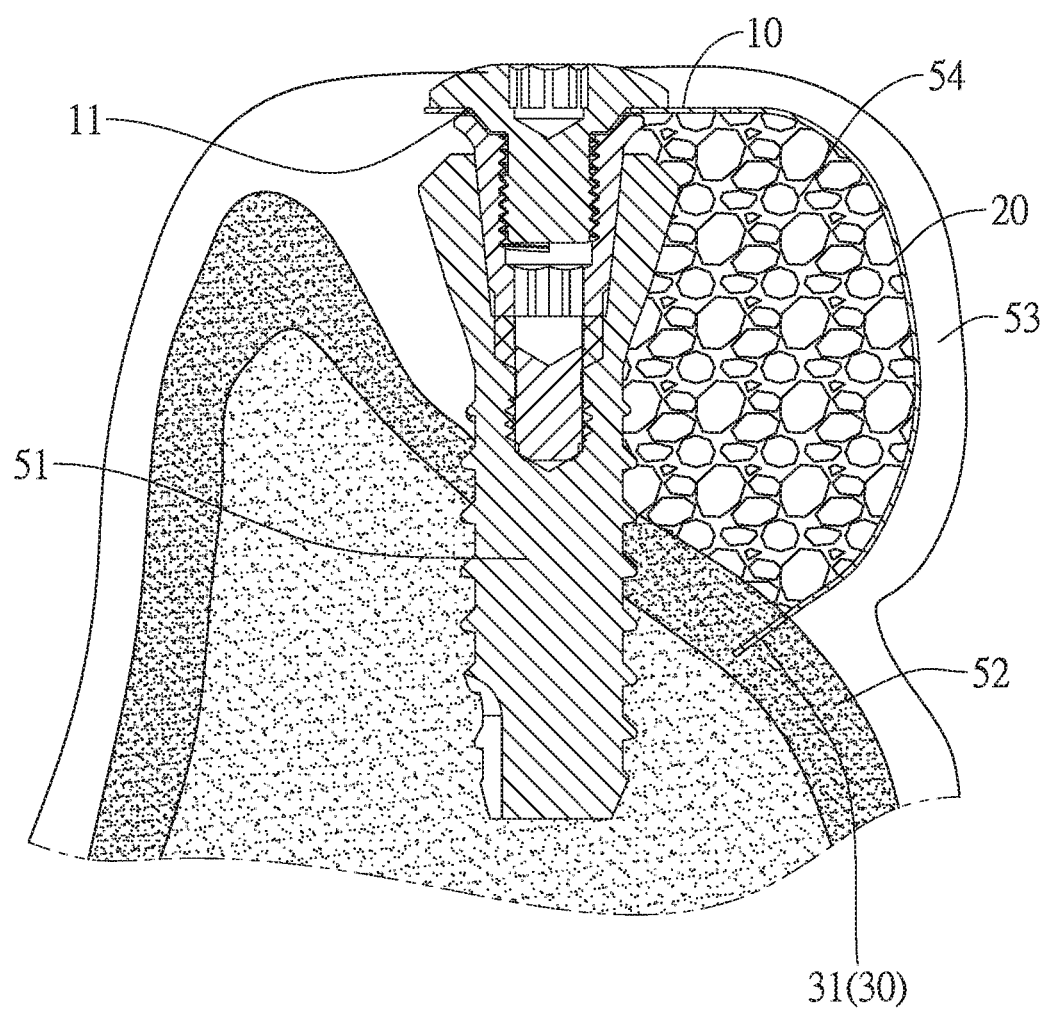
FIG. 3 is an applied cross-sectional view of the preferred embodiment of the present invention, showing it installed at an edentulous site together with an artificial toothroot.
Figure 4:
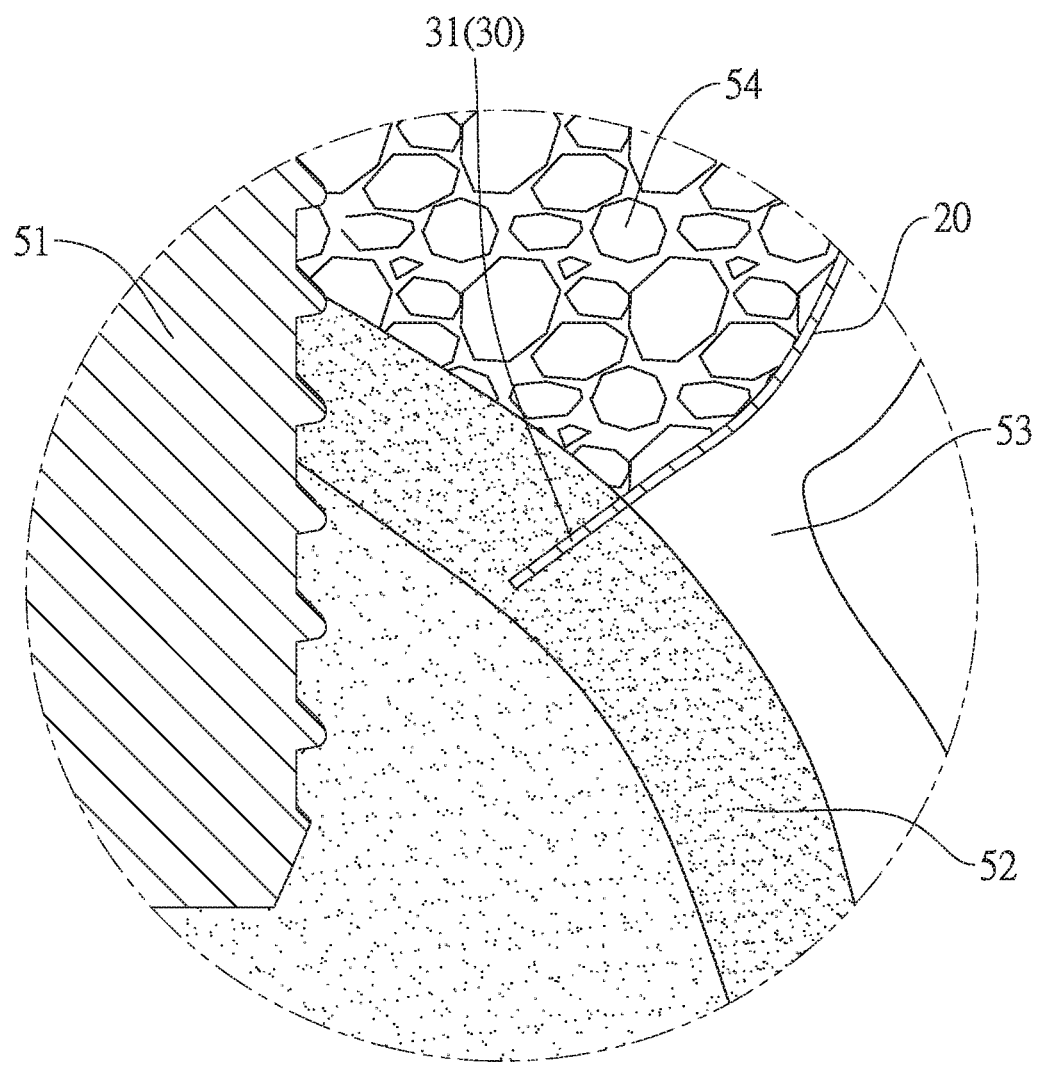
FIG. 4 is a partial, enlarged view of FIG. 3, showing how a fixing portion is inserted into and fixed to osseous tissue.
Figure 5:
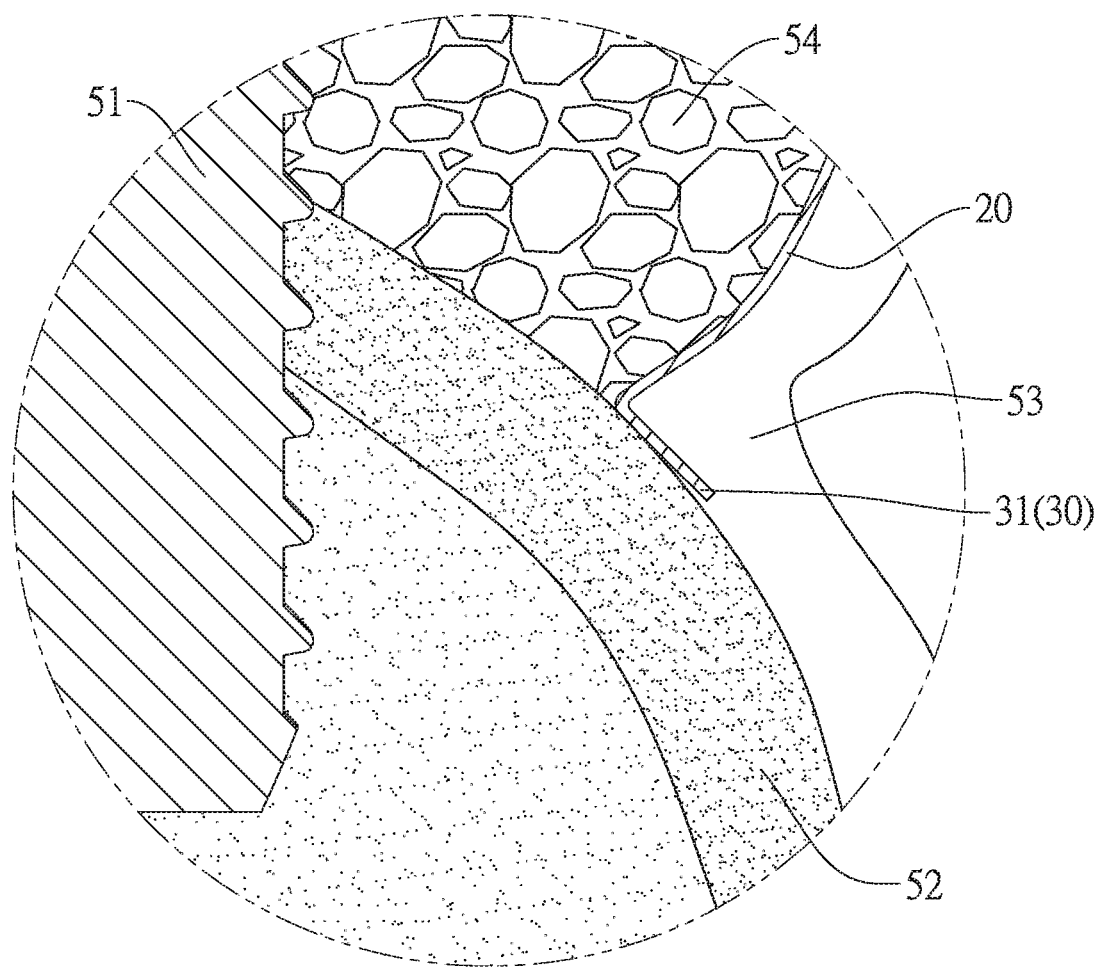
FIG. 5 is a partial, enlarged view of FIG. 3, showing how the fixing portion is inserted and fixed between osseous tissue and soft tissue.

Referring to FIG. 3, the disclosed alveolar membrane is to be used as the conventional alveolar membranes, where the through hole 11 of the connecting portion 10 is combined with an artificial toothroot 51 screwed into osseous tissue 52 at an edentulous site. The capping portion 20 caps the osseous graft 54. What makes the present invention different is that the digits 31 of the fixing portion 30 are inserted into osseous tissue 52 (FIG. 4) or between osseous tissue 52 and soft tissue 53 (FIG. 5). Thereby, with the connecting portion 10 and the fixing portion 30 at its two ends of fixed to the artificial toothroot 51 and human tissue respectively, the disclosed alveolar membrane provides good fixation that ensures an osseous graft 54 to be firmly fixed to the predetermined site, thereby contributing to smooth dental implant surgery.

The present invention is advantageous for its simple structure and high practicality. Since the alveolar membrane has its both ends equipped with fixing features, it can firmly fix an osseous graft to a predetermined site, thereby contributing to smooth dental implant surgery.

What is claimed is:

1. An alveolar membrane, comprising:
   a connecting portion, being provided with a through hole for an artificial toothroot to pass therethrough, and a connecting section;
   a capping portion, having its one end connected to the connecting portion and including a plurality of openings, the connecting section is located between the through hole and the capping portion to leave a distance between the through hole and the capping portion; and
   a fixing portion, being located at an opposite end of the capping portion and having at least one digit that includes a tip to be fixed at a predetermined site in human tissue, the at least one digit is in a sharp shape and has two oblique edges, and the two oblique edges are interconnected at the tip;
   wherein the connecting portion has its width gradually increased from its one end toward the capping portion until its width is equal to that of the capping portion, and a flexible portion is provided at a joint between the capping portion and the fixing portion, in which the flexible portion is formed by a plurality of slots arranged into a straight line;
   the digit of the fixing portion is configured to be inserted into osseous tissue or between osseous tissue and soft tissue.

2. The alveolar membrane of claim 1, wherein the connecting portion, the capping portion and the fixing portion are formed in a single sheet.

3. The alveolar membrane of claim 1, wherein a flexible portion is provided at a joint between the connecting portion and the capping portion.

4. The alveolar membrane of claim 3, wherein the flexible portion is formed by a plurality of slots arranged into a straight line.

\* \* \* \* \*